(12) United States Patent
Kärnerud et al.

(10) Patent No.: US 6,406,708 B1
(45) Date of Patent: Jun. 18, 2002

(54) THERAPEUTIC COMPOSITIONS

(75) Inventors: Lars Kärnerud, Tenhult; Stellan Ölmeskog, Aneby, both of (SE)

(73) Assignee: Interhealth AB, Huskvarna (SE)

( * ) Notice: Subject to any disclaimer, the term of this patent is extended or adjusted under 35 U.S.C. 154(b) by 0 days.

(21) Appl. No.: 09/700,215

(22) PCT Filed: May 12, 1999

(86) PCT No.: PCT/SE99/00819
§ 371 (c)(1),
(2), (4) Date: Nov. 13, 2000

(87) PCT Pub. No.: WO99/58104
PCT Pub. Date: Nov. 18, 1999

(30) Foreign Application Priority Data

May 12, 1998 (SE) ................................................ 9801647

(51) Int. Cl.⁷ ............................. A61K 7/00; A61K 7/48; A61K 7/40
(52) U.S. Cl. .................... 424/401; 424/78.07; 424/404; 424/65; 514/887; 514/859; 514/252
(58) Field of Search ....................... 424/401, 65, 78.07, 424/404; 514/252, 859, 887

(56) References Cited

U.S. PATENT DOCUMENTS

| | | | |
|---|---|---|---|
| 5,079,003 A | | 1/1992 | Scaffidi |
| 5,476,852 A | * | 12/1995 | Cauwenbergh ............. 514/252 |
| 5,643,584 A | * | 7/1997 | Farng et al. ................ 424/401 |
| 5,646,131 A | | 7/1997 | Badwan et al. |
| 5,702,710 A | * | 12/1997 | Charpentier et al. ........ 424/401 |
| 5,879,666 A | * | 3/1999 | Lucas et al. ................. 424/65 |
| 6,162,448 A | * | 12/2000 | Nguyen et al. ............. 424/401 |

FOREIGN PATENT DOCUMENTS

| | | |
|---|---|---|
| EP | 0 366 154 A2 | 5/1990 |
| EP | 0 457 193 A2 | 11/1991 |
| WO | WO 94/21225 A1 | 9/1994 |
| WO | WO 95/04537 A1 | 2/1995 |
| WO | WO 96/11572 A1 | 4/1996 |
| WO | WO 96/21422 A1 | 7/1996 |
| WO | WO 98/22083 A1 | 5/1998 |

OTHER PUBLICATIONS

Patent Abstracts of Japan, "JP 61–227517 A, Lion Corp., published Oct. 9, 1986", vol. 11, No. 69 C–407.
Patent Abstracts of Japan "10–087458 A, Lion Corp., published Apr. 7, 1998".
Patent Abstracts of Japan, "JP 07–138125 A," Shiseido Co. Ltd., published May 30, 1995, vol. 95, No. 5.
Hoffmann SL et al, "Safety, Immunogenicity, And Efficacy Of A Malaria Sporozoite Vaccine Administered With Monophosphoryl Lipid A, Cell Wall Skeleton Of Mycobacteria, And Squalane As Adjuvent" Am J Trop Med Hyg, 51(5), pp. 603–612, Nov. 1994. Abstract.
Allison AC, "Adjuvants and Immune Enhancement" Int. J. Technol. Assess Health Care, 10(1), pp., 107–120, Winter 1994. Abstract.
Stone HD et al., "Efficacy of Experimental Newcastle Disease Water–In–Oil Oil–Emulsion Vaccines Formulated from Squalane and Squalane. "Avian Dis. 34(4), pp. 979–983, Oct.–Dec. 1990.

* cited by examiner

Primary Examiner—José G. Dees
Assistant Examiner—Mina Haghighatian
(74) Attorney, Agent, or Firm—Browdy and Neimark

(57) ABSTRACT

The invention relates to a composition comprising, from 2 to 8% squalane, from 1.5 to 8% cyclodextrin, and from 1.5 to 8% of a pharmaceutically and/or cosmetically acceptable acid selected from aliphatic mono-, di- and α-hydroxy carboxylic acids having from 2 to 10 carbon atoms, and the balance selected from other pharmaceutically and/or cosmetically acceptable compatible anti-acne active substances as well as pharmaceutically and/or cosmetically acceptable paste, ointment or cream bases and additives. The composition has therapeutic and cosmetic effect and can be used as a cosmetic as well as for the preparation of a drug for prophylactic and curative treatment of acne. A method for the preparation of the composition as well as a method for treatment of acne is also included in the invention.

11 Claims, No Drawings

THERAPEUTIC COMPOSITIONS

CROSS REFERENCE TO RELATED APPLICATION

The present application is the national stage under 35 U.S.C. 371 of PCT/SE99/00819, filed May 12, 1999.

The present invention relates to a new composition for topical application comprising squalane, cyclodextrin, and from 1.5 to 8% of a pharmaceutically and/or cosmetically acceptable aliphatic mono-, di- and α-hydroxy carboxylic acid having from 2 to 10 carbon atoms. The balance is selected from other compatible pharmaceutically and/or cosmetically acceptable active substances used for the treatment of acne and pharmaceutically and/or cosmetically acceptable paste, ointment or cream bases and additives. Further included is a method for the preparation of the new compositions as well as a method of treatment of acne. The composition may be used as a cosmetic or therapeutic, and for the preparation of a drug for treatment of diseases caused by attacks of micro-organisms, especially for the treatment of acne.

BACKGROUND OF THE INVENTION

Within the cosmetic field squalane $C_{30}H_{62}$ has been used as skin lubricants in cosmetic and hygienic preparations and as fixatives in perfumes, in concentrations of up to 50%.

U.S. Pat. No. 5,079,003 to Schadiffi A., discloses creams or lotions comprising emulsions of fish oils, such as shark liver oil, squalane, and squalene, used as moisturisers, as bases for cosmetics, as hand and body lotions and as sunburn preventives. Compositions are described also comprising numerous other ingredients with therapeutic and synergistic effects on the skin.

Within the therapeutical field, squalane as well as squalene have been used as penetration enhancers of actives, and in adjuvants of vaccines (see e.g. Hoffman S L et. al. Am J Trop Med Hyg 1994 November; 51(5): 603–12). As components of oil-emulsion based adjuvants in injection preparations they are considered to have anti-irritating properties (see e.g. Stone H D et. al. Avian Dis 1990 October––December; 34(4): 979–83), and as such they also have shown an immunostimulating effect (Allison A C, Int J Technol Assess Health Care 1994 Winter; 10(1): 107–20). Moreover, they both are deemed to have a proliferation stimulating effect on the dermal as well as the muscular tissues.

Cyclodextrin is a molecule capable of forming an inclusion complex with squalane. In this type of complex cyclodextrin plays the role of a "host molecule", forming a cavity lodging one or several "guest molecules". In a work intituled "Cyclodextrin Chemistry" (Ed. Springer Verlag 1978) it is stated that the cavity of the cyclodextrin molecule has a calculated diameter of 7 Å and a depth of 7 Å. This may be correlated to the diameter of the "guest molecule", which for the squalane molecule can roughly be estimated to 5 Å and 30–35 Å respectively.

Our co-pending patent application WO9822083A1 (claiming priority from our co-pending application SE 9604193-4, filed Nov. 15, 1996) relates to compositions comprising as active ingredient (i) one or several components derived from an extract of crude shark liver oil, including squalane, and (ii) one or several carbohydrates forming inclusion and/or chelate complex, including cyclodextrin, with (i) and optionally (iii) one or several non-shark liver oil derived therapeutically or cosmetically active agents. In the Example also 0.15% by weight of sorbic acid is included as a preservative.

WO9421225A1 relates to a skin care composition comprising a conjugate of vitamin A derivative and β-cyclodextrin for therapeutic or prophylactic treatment of ageing symptoms in skin.

Patent Abstracts of Japan, Vol. 11, No. 69, C-407, abstract of JP 61-227517 A and the European patent 0 366 154 disclose cosmetic compositions comprising cyclodextrin derivatives and squalane.

However, prior art gives no information about the new and unexpected advantages on the treatment of acne, obtained by the addition, to a composition, for topical application, comprising squalane and cyclodextrin, of from 1.5 to 8% of a pharmaceutically and/or cosmetically acceptable aliphatic mono--, di- and α-hydroxy carboxylic acids having from 2 to 10 carbon atoms. According to our findings an amount as low as 0.15% of sorbic acid does not give any anti-acne effect.

DESCRIPTION OF THE INVENTION

The present invention relates to a composition, for the treatment of acne, comprising from 2 to 8% of squalane, from 1.5 to 8% of cyclodextrin, and from 1.5 to 8% of a pharmaceutically and/or cosmetically acceptable aliphatic mono-, di- and α-hydroxy carboxylic acid having from 2 to 10 carbon atoms, and wherein the balance is selected from other compatible pharmaceutically and/or cosmetically acceptable anti-acne active substances and pharmaceutically and/or cosmetically acceptable paste, ointment or cream bases and additives. The composition may be used as a cosmetic or a drug, that creates an environment wherein the growth of pathogenic micro-organisms is repressed to the advantage of the growth of more innocuous micro-organisms. The invention further includes a method for the preparation of the compositionas well as a method of treatment of acne. The term "pharmaceutically and/or cosmetically acceptable" is meant to state that the amounts of the agent in question should be pharmaceutically and/or cosmetically acceptable.

According to established scientific apprehension acne is caused by an increased sebum production, clogging of the pores, and an inflammation caused by the bacterium Propionibactrium acnes. The increased sebum production is due to an increased testosterone production during the puberty. The testosterone stimulates an increase of the size of the sebum glands and an increased sebum production.

Acne rosacea is a chronic disease affecting the skin of the nose, forehead, and cheeks marked by flushing, followed by red coloration due to dilatation of the capillaries, with the appearance of papules and acne-like pustules.

Specifically the new composition, which are defined in the appended claims, have a prophylactic and curative effect on disorders of the skin such as acne and can be used as a drug or a cosmetic preparation for prophylactic or curing treatment of acne.

The complex squalane/cyclodextrin has a healing and anti-inflammatory effect which, in combination with the "antibacterial" effect obtained by the addition of an acid lowering the pH of the composition to a value that suppress the growth of pathological micro-organisms and supports the growth of more innocuous micro-organisms gives a drug for local application to the skin having unexpected excellent properties on the skin condition mentioned above. Preferred acids are the α-hydroxy acids, especially lactic acid and azelaic acid.

Also treatment of rosacea with the composition according to the invention has shown excellent results with diminished reddening, papules, and pustules already after application of the composition for only a few days.

Pharmaceutically and/or cosmetically acceptable aliphatic mono-, di- and α-hydroxy carboxylic acids according to the invention are selected from propionic, butyric, valeric, hexanoic, heptanoic, octanoic, nonanoic and decanoic acid and any isomers thereof; oxalic, malonic, succinic, glutaric, fumaric acid; adipic, pimelic, suberic, azelaic, sebacic acid; glycolic, lactic, malic, tartaric, citric and gluconic acid. Especially preferred are azelaic acid, lactic acid, and the other saturated and unsaturated aliphatic α-hydroxy acids (AHA-acids).

The acids might suitably be included in the composition according to the invention in an amount of 1.5 to 8%, preferably 2 to 7% and most preferably 2.5 to 5%.

The composition according to the invention may also contain up to 0.15% of sorbic acid as a preservative.

Squalane is a softening substance moisturising dry skin in a natural way. It adds fat to the skin without causing a fatty feeling on the skin. Squalane might be included in the composition according to the invention in an amount of 2 to 8%, preferably 3 to 7% and most preferably 4 to 6%.

Cyclodextrin consists of 5, 6 or 7 α-1,4 connected glucose units (α- β- γ-cyclodextrin) and is further described above. Cyclodextrin might be included in the composition in an amount of 1.5 to 8%, and preferably 2 to 7%.

By combining squalane with cyclodextrin an inclusion or chelate complex is formed which in combination with the above mentioned acids gives a pharmaceutical or cosmetic having an unexpected effect.

The compositions may be formulated as an ointment, a cream, a gel, a milk, a lotion and a powder. Suitable cosmetically and pharmaceutically acceptable bases and actives are e.g. shorea butter as well as the actives mentioned below.

One example of a suitable fat substance is Shorea butter. It is a natural triglyceride, from the nuts of the tropical tree Shorea Stenoptera, sometimes used to moderate an optional inclination to irritation of other components in cosmetics. Shorea butter gives a pleasant, silky feeling to the skin and enhances further the effect of the composition by its beneficial effect on the skin and might be included in an emulsifying amount such as up to 10%. Shorea butter has an anti-acne and anti-inflammatory effect, related to the content of sterols, enhancing the effect of the composition according to the invention.

Starch are substances giving a pleasant feeling to the skin and aids in eliminating the fatty feeling which easily is achieved at the application of ointments and creams to the skin. Starch might be included in an amount up to 10%.

For the emulsifying process, corn starch based emulsifiers are chosen which have an extremely low tendency to irritation. Said type of emulsifiers is used for cosmetics to be used in the vicinity of the eyes.

Examples of substances compatible with squalane as well as cyclodextrin are, for the treatment of acne are, e.g. Vitamin A acid, benzoyl peroxid, and clindamycin. A further preferred active is shorea butter.

The therapeutically and cosmetically acceptable actives might be included in for the man skilled in the art well known therapeutically and cosmetically effective dosages.

The invention also provides a method of preparing the compositions according to the invention. This method comprises the addition of a water phase, obtained by admixing cyclodextrin, organic acid and preservatives, and a water base under heating and agitation, to an oil phase comprising the squalane component, agitating and, if necessary heating until a homogenous emulsion of the two components is achieved, and optionally adding the pharmaceutically and/or cosmetically acceptable components to the emulsion. The water-soluble substances, whether active or additives, are added to the water phase and the oil soluble to the oil phase.

The heating temperature will be the one giving, in combination with the agitation, a homogenous emulsion of the components of the composition. Such a range can be from just above room temperature, such as 30° C., to an upper limit, of e.g. 90° C. The temperature must be selected to guarantee that the fat phase is in a liquid state. Obviously, the upper limit of the heating temperature is set by the boiling point of the mixture, but care should also be taken not to decompose unduly the components of the mixture by excessive heating.

The hydrophilic medium used to dissolve the cyclodextrin may comprise water or a pharmaceutically and/or cosmetically acceptable alcohol such as ethanol, propylene glycol, and various suitable mono-, di- and trihydric alcohols, conventional to the art, as well as mixtures of any of these, in an amount up to 20%.

Any lipophilic medium used to dissolve the lipophilic, i.a. hydrophobic component, may comprise a pharmaceutically and/or cosmetically acceptable vegetable oil, or any lipid cream basis such as conventionally used within the field of the art.

Depending on the relative amounts of the aqueous and oily phases, an ointment, a cream, a gel, a milk or a lotion will be obtained, as will be known to the man skilled in the art.

The invention will now be further illustrated by way of the following non-limiting examples.

In this application all parts and percentages are by weight unless otherwise stated.

EXAMPLE 1

An ointment for the treatment of acne is prepared from the following ingredients:

| PHASE A (oil phase) | |
|---|---|
| Cremeol FR 36 | 5.60% |
| Cremeol SH | 2.00% |
| Ascorbylpalmitate | 0.01% |
| Glucamate SSE20 | 1.80% |
| Glucate SS | 1.20% |
| Squalane | 6.00% |
| PHASE B (water phase) | |
| Water | 67.24% |
| Sorbic acid | 0.15% |
| Cyclodextrin | 6.00% |
| Lactic acid | 5.00% |
| Corn PO4PH "B" | 5.00% |
| Total | 100.0% |

The oil phase is heated under agitation to 75° C. The water phase is heated under agitation to 75° C. To obtained the preserving effect, sorbic acid is added to the water and should be completely dissolved before the addition of cyclodextrin.

The water phase is slowly added to the oil phase under agitation. The ointment is cooled under agitation. At about 50° C. the starch (Corn PO4 PH "B") is added.

EXAMPLE 2

A skin care cream for the prophylactic treatment of acne is prepared from the following ingredients:

| PHASE A (oil phase) | |
|---|---|
| Cremeol FR 36 | 5.60% |
| Cremeol SH | 4.00% |
| Ascorbylpalmitate | 0.01% |
| Glucamate SSE20 | 1.80% |
| Glucate SS | 1.20% |
| Squalane | 6.00% |
| PHASE B (water phase) | |
| Water | 70.74% |
| Sorbic acid | 0.15% |
| Cyclodextrin | 6.00% |
| Lactic acid | 1.50% |
| Corn PO4PH "B" | 3.00% |
| Total | 100.0% |

The oil phase is heated under agitation to 75° C. The water phase is heated under agitation to 75° C. To give the preserving effect sorbic acid is added to the water and should be completely dissolved before the addition of cyclodextrin.

The water phase is slowly added to the oil phase under agitation. The ointment is cooled under agitation. At about 50° C. the starch (Corn PO4 PH "B") is added.

The chemical definitions of the substances referred to by their trademarks are as follows:

Cremeol™ FR 36: $C_{16}$-$C_{18}$ mono-, di-, and triglycerides;

Cremeol™ SH: Shorea butter CAS no. 91770-65-9 (Botanical classification Shorea stenoptera)

Glucamate™ SSE 20: PEG-20 methyl glucose sesquistearate;

Glucate™ SS: methyl glucose sesquistearate

CORN PO4 PH "B"™: Cross-linked di-starchphosphate based on corn starch.

The Cremeol™ series are commercially available from Aarhus oljefabrik A/S, of Aarhus, Denmark.

The Glucate™ SS and Glucamate™ SSE 20 are commercially available from Amerchol Corporation, of Edison, USA.

CORN PO4 PH "B"™ is commercially available from Dr. HAUSER GMBH, of Garmisch-Partenkirchen, Germany.

A pilot study was performed during 6 weeks on 11 subjects suffering from acne. Thereof, 8 have had acne for a time period of between 0.5 to 3 years and 3 more than 10 years. The preparation was applied twice a day, each time, in an absorbable amount. The results were as follows:

| Subject | Age | Beginning of treatment. Date | Intensity of complaints | Result of treatment | Comments (98 08 25) |
|---|---|---|---|---|---|
| A | 32 | 98 05 20 | Slight | Free of complaints | Rapid complete cure (approx. 1 week) |
| B | 16 | 98 07 08 | Moderate | Free of complaints | Rapid complete cure (approx. 1 week) |
| C | 34 | 98 06 20 | Severe | Good | Reduction of acne, curing of scar tissue |
| D | 40 | 98 07 20 | Moderate | Good | Still a certain degree of acne |
| E | 35 | 98 02 15 | Severe | Good | Has still occasional spots of acne |
| F | 16 | 98 07 16 | Moderate | Free of complaints | |
| G | 16 | 98 04 16 | Severe | Interrupt the treatment | The treatment had initially a good effect. After interruption of the treatment the acne recurred. |
| H | 45 | 98 08 17 | Slight | Free of complaints | Rapid complete cure (approx. 1 week). Overall skin improvement |
| I | 35 | 98 07 16 | Severe | Free of complaints | |
| J | 28 | 98 07 15 | Slight | Slightly better | Initially the acne get slightly worse. Later the acne was improved. |
| K | 24 | 98 01 15 | Severe | Free of complaints | Rapid complete cure, no acne left after 4 months. |

Especially surprising is that 2 of the subjects that had suffered from acne for more than ten years were completely cured within 14 days.

What is claimed is:

1. A method of treatment of acne by local application to the skin of a human in need thereof, of an effective amount of a composition comprising (1) anti-acne active ingredients consisting essentially of (a) from 2 to 8% squalane, (b) from 1.5 to 8% cyclodextrin, and (c) from 1.5 to 8% of a pharmaceutically and cosmetically acceptable carboxylic acid which comprises an aliphatic mono-, di- and α-hydroxy carboxylic acid having from 2 to 10 carbon atoms; and (2) a pharmaceutically and therapeutically acceptable cream base.

2. The method according to claim 1, wherein the carboxylic acid is selected from the group consisting of propionic acid, butyric acid, valeric acid, hexanoic acid, heptanoic acid, octanoic acid, nonaoic acid, decanoic acid, oxalic acid, malonic acid, succinic acid, glutaric acid, fumaric acid, adipic acid, pimelic acid, suberic acid, azelaic acid, sebacic acid, glycolic acid, lactic acid, malic acid, tartaric acid, citric acid and gluconic acid.

3. The method according to claim 1, wherein the acid is an α-hydroxy carboxylic acid selected from the group consisting of glycolic acid, lactic acid, malic acid, tartaric acid, citric acid and gluconic acid.

4. The method according to claim 1, wherein the acid comprises azelaic acid or lactic acid.

5. The method according to claim 1, wherein the acid comprises azelaic acid.

6. The method according to claim 1, wherein the carboxylic acid is a monocarboxylic acid selected from the group consisting of propionic acid, butyric acid, valeric acid, hexanoic acid, heptanoic acid, octanoic acid, nonanoic acid, decanoic acid, and any isomer thereof.

7. The method according to claim 1 wherein the carboxylic acid is a dicarboxylic acid selected from the group consisting of oxalic acid, malonic acid, succinic acid, glutaric acid, fumaric acid, adipic acid, pimelic acid, suberic acid, azelaic acid, and sebacic acid.

8. The method according to claim 1, wherein the cream base comprises shorea butter.

9. The method according to claim 1, wherein said squalane is present in an amount of from 3 to 7%.

10. The method according to claim 9, wherein said cyclodextrin is present in an amount of 2–7%.

11. The method according to claim 10, wherein said squalane is present in an amount of 4–6%.

* * * * *